United States Patent [19]

Tokita et al.

[11] Patent Number: 4,584,991
[45] Date of Patent: Apr. 29, 1986

[54] MEDICAL DEVICE FOR APPLYING THERAPEUTIC RADIATION

[76] Inventors: Kenneth M. Tokita, 1408 Via Arco, Palos Verdes Estates, Calif. 90274; Belmont L. Haller, 3279 Cedar Ave., Long Beach, Calif. 90806

[21] Appl. No.: 561,879

[22] Filed: Dec. 15, 1983

[51] Int. Cl.$^4$ .............................................. A61N 5/12
[52] U.S. Cl. ...................................... 128/1.1; 128/1.2
[58] Field of Search ..................... 128/1.1, 1.2; 604/20, 604/21

[56] References Cited

U.S. PATENT DOCUMENTS

| | | | |
|---|---|---|---|
| 1,603,767 | 10/1926 | Harris | 128/1.1 |
| 3,224,432 | 12/1965 | Billingsley | 128/1.2 |
| 3,351,049 | 11/1967 | Lawrence | 128/1.2 |
| 3,505,991 | 4/1970 | Hellerstein et al. | 128/1.1 |

FOREIGN PATENT DOCUMENTS 857992  1/1961  United Kingdom ................ 128/1.2

OTHER PUBLICATIONS

Swanberg, Improved Uterine Radiation Applicator, Am. Jrnl. Surg., Apr., 1930, pp. 862–865.

Primary Examiner—Edward M. Coven
Attorney, Agent, or Firm—Don B. Finkelstein

[57] ABSTRACT

This device for applying therapeutic radiation serves as a carrier for a selected radiation source that can be inserted into the device to provide a controlled intensity and location of the radiation source. The device can then be inserted into any bodily canal and oriented to bring the radiation source into close proximity to that portion of the bodily canal requiring therapeutic radiation treatment. The location of the radiation source within the device is possible because the device contains a criss-cross, non-intersecting pattern of channels internal to the device. The radiation source can be positioned at any location along any of the channels. The device can be constructed of several members so that a number of members can be connected to form a device of the desired length.

17 Claims, 6 Drawing Figures

MEDICAL DEVICE FOR APPLYING THERAPEUTIC RADIATION

BACKGROUND OF THE INVENTION

1. Field of the Invention

This invention relates to arrangements for the application of therapeutic radiation and, more particularly, to an improved device for applying therapeutic radiation internally through bodily orifices.

2. Description of the Prior Art

Application of therapeutic radiation has required an array of arrangements to be responsive to the large variety of possible configurations. This array has been composed mainly of shaping the radiation source for the particular application. A therapeutic radiation source that is presently available is formed in a linear configuration of a wire-like member with small cylindrical sleeves placed in a spaced apart array on the wire. Each cylindrical sleeve contains a radiation source. The intensity of the radiation can be controlled by preselecting the number and spacing of the sleeves. The wire-like member and sleeves are generally encapsulated in a plastic coating to define a flexible, elongated radiation source. This radiation source gives the appearance of an insulated electric wire.

Prior to the present invention, this radiation source was formed into a coil or a loop and applied to the portion of the body requiring therapeutic radiation treatment. The coil or loop was brought into close proximity to the part of the body requiring therapeutic radiation treatment. Such method of application was functionally acceptable for parts external to the body as the coil or loop could be placed directly over the area requiring therapeutic radiation with minimal radiation being applied to other parts of the body. However, in those applications wherein the portion of the body requiring therapeutic radiation was accessible through any one of the bodily orifices, the entire area surrounding the coil or loop was radiated in addition to the desired, particular body portion. Further, it was difficult to configure a coil or loop and apply it in situations such as in the treatment of the cervix through the vagina.

Due to the dangers of exposing healthy tissue to unnecessary doses of radiation, there has long been a need for an improved device to control the application of therapeutic radiation in both intensity and direction when applied through a body orifice inside a bodily canal as well as providing a stable holder to control the direction and intensity of radiation applied externally to any area of the body requiring therapeutic radiation treatment.

One of the most desirable features of an improved therapeutic radiation device is to allow controlled application deep inside any bodily canal with a certainty that the radiation source will not become uncoiled as it has in the prior art when the radiation source is in the form of the above mentioned wire, was coiled and internally applied. In the prior art a loop of the wire-like radiation source often would become twisted around the very instrument used to apply the loop internally. The user must be assured that the prescribed intensity of radiation will be applied as desired without the change that the radiation source would be shielded from the treated area by the very same instrument used to insert the radiation source.

Another desirable feature is that the improved application device should be constructed to provide a continuous smooth peripheral surface to the inside walls of the bodily canals. Whereas the covering of the radiation source and the instrument used in the prior art for application may each individually be smooth, the combination often did not provide an overall smooth surface with consequent irritation to delicate membranes internal to the bodily canal during the application of a coil or loop of radiation source.

A further desirable feature is the ability of the improved application device to be fashioned from material that may be sterilized. This feature allows a sterile surface to be applied inside a bodily canal. Even though the radiation source available in the prior art could be sterilized and applied as a coil or loop in an antiseptic manner, the repeated handling of the radiation source to form it into a coil or a loop before insertion increased the probability of loss of antiseptic quality. The prior art application devices required the radiation source to be handled as it is inserted into the device but if such insertion can be accomplished without degregating the antiseptic environment of the outside surface of the device and if the application device is fashioned such that the surface of the radiation source does not come in contact with the body, such a device minimizes the efforts necessary to maintain an antiseptic environment.

Yet another desireable feature is a one piece body member of a diameter and length that can be easily accepted by a bodily orifice and inserted to the desired depth. However, to allow versatility in treatment and decrease the weight of the instrument that is inserted into a bodily canal, the application device can be made up of attachable members. The members must be securely attached together. Attachable members can be added until the application device is of the desired length which is particularly useful when the treatment involves small bodily orifices to such as the nasal or ear canals. The construction of separate members from inexpensive material with the subsequent assembly of the members in the desired length provides an econimical system should the user wish to use an assembled device once and then dispose of it.

SUMMARY OF THE INVENTION

Accordingly, it is an object of this improved device to provide a controlled configuration for the application of a radiation source by a body member that presents a sterile surface to the internal walls of a bodily canal or external body surface. It is another object to provide an application device constructed of material to allow the user to maneuver the device into position without twisting or folding.

A further object is to provide an application device that is inexpensive should the user desire to dispose of it after one use.

The above and other objects are achieved in the present invention by construction of the application device in any geometric form with a preferred body member being one that presents a smooth, contiguous, peripheral surface for the portion to be inserted into a bodily canal. Each application device of the present invention is provided with a plurality of internal generally U-shaped channels traversing the application device near its outside surface and accessible through one end surface of the member. It is desirable that the channels provide a criss-cross pattern near the entire outer surface without intersecting any other channel. This allows the insertion of the radiation source into a particular channel without the chance that the radiation source would be diverted along any other channel, become lodged in the transition from one channel to another or block another radiation source inserted into any other channel.

To achieve the object of versatility in treatment, the application device of the present invention may be constructed as attachable body members. The body members may then be connected together with the internal channels aligned so that, when the radiation source is inserted into the channel, the radiation source will easily transition from one member to another until the desired location of the radiation source in the U-shaped channel is achieved. Once a radiation source is inserted to any desired position along any channel, additional radiation sources may then be inserted to any position along any other channel so that the radiation source may be grouped to provide the required intensity. By selecting the channels that are used, the radiation source may provide radiation only along one side, only at the end of the application device, or in any desired pattern. Once the radiation source is formed within the application device, the configuration is preserved even though inserted into a bodily canal. Thus, the user can control the orientation of the radiation to bring the radiation source in close proximity with only that predetermined portion of the body requiring therapeutic radiation treatment even if located deep inside a bodily canal. As can be readily seen, this control of therapeutic radiation can be utilized externally to the body as well as internally.

BRIEF DESCRIPTION OF THE DRAWINGS

The above and other embodiments of the present invention may be more fully understood from the following detailed description, taken together with the accompanying drawing wherein similar reference characters refer to similar elements throughout and in which.

DETAILED DESCRIPTION OF THE PREFERRED EMBODIMENT

Figure 1:
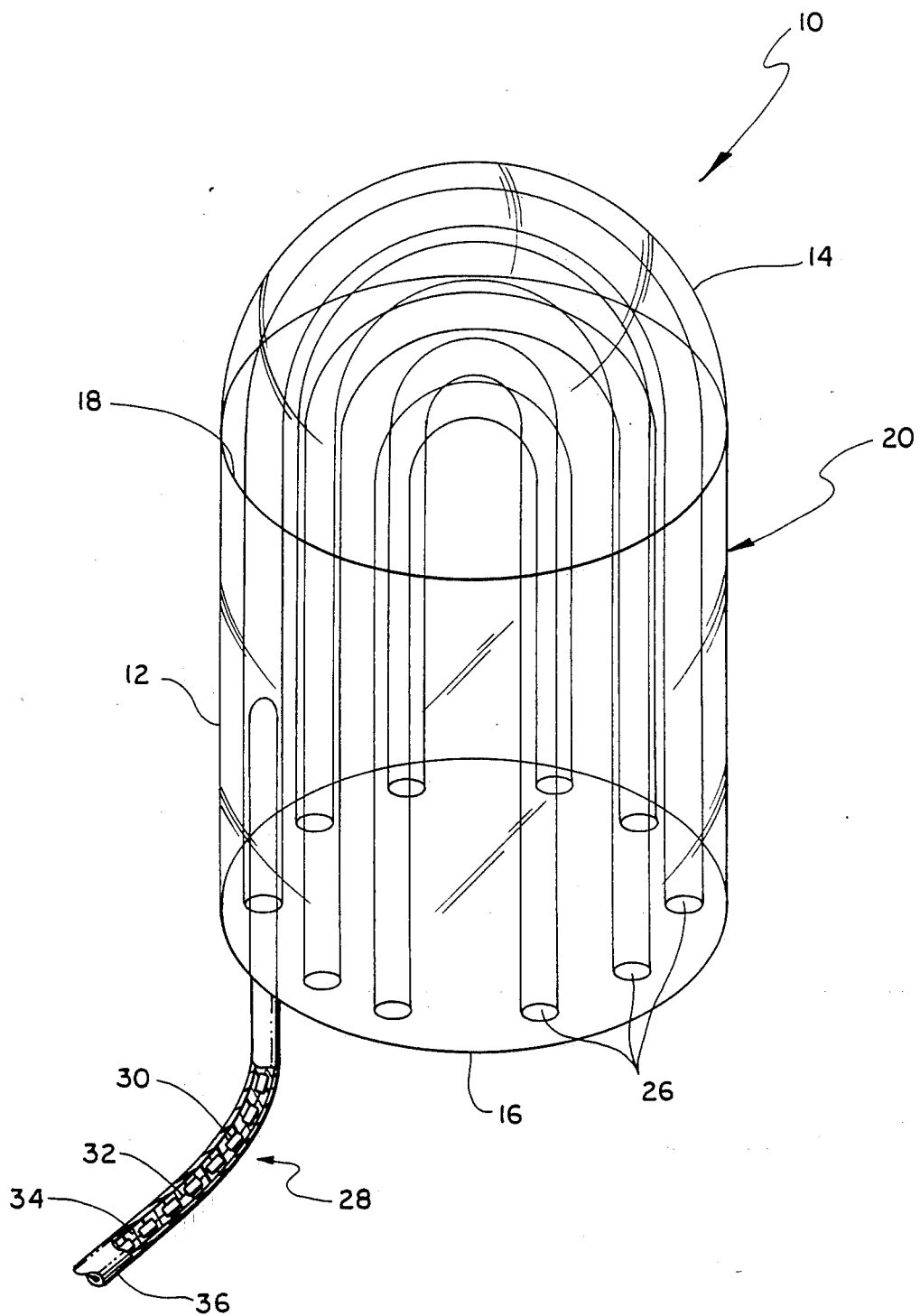
FIG. 1 illustrates a preferred embodiment of the present invention showing the body member of an application device with a plurality of internal U-shaped channels and a radiation source partially inserted into one of the channels.

Referring now to the drawings, there is illustrated in FIG. 1 a preferred embodiment, generally designated 10, of the improved device for applying therapeutic radiation. The application device 10 consists of a body member 20 having a peripheral surface consisting of a cylindrical section 12 ending in a closed double curved surface, which in the preferred embodiment is a dome 14 mounted on the first end surface 18 of the cylinder and a spaced apart second end surface 16. The application device 10 can be formed of material such as polyethylene, polystyrene, polypropylene or any moldable plastic. The preferred embodiment uses a clear material so that the position of the radiation source 28 inside the holding means application device 10 can be readily ascertained. The size of the cylindrical section 12 is determined by the use to which the particular device 10 will be applied. If the device 10 is to be inserted into a bodily canal that does not expand such as the nasal or ear canal, then an outside diameter for the cylindrical section 12 would be selected based upon the average diameter of such canals for adults. The diameter of the cylindrical section 12 would be selected in a similar manner when the device 10 is used to treat children or infants. The axial length of the cylindrical section 12 is selected upon the basis of which bodily canal will be entered during the treatment. For the nasal or ear canal, the axial length would be selected to provide access along the entire canal plus an additional length to directionally control the insertion and orientation of the device 10. By selecting the minimum length required, the final weight of the device 10 can be lessened so that the application of the device 10 will not produce undue pressure along delicate canals.

In order to allow comfortable insertion of the device 10 into a bodily canal, the first end surface 18 of the cylindrical section 12 is terminated by a dome 14. The radius of the dome 14 should be similar to the radius of the cylindrical section 12 in order to provide a smooth transition of the peripheral surface between the dome 14 and the cylindrical section 12.

In order to allow the device 10 to be used for a wide variety of treatment, the cylindrical section 12 and dome 14 are provided with walls forming a pattern of criss-cross channels 26 that internally traverse the device 10 at a preselected distance from the peripheral surface. The channels 26 can be configured as shown to traverse the device 10 without intersecting each other.

Figure 2:
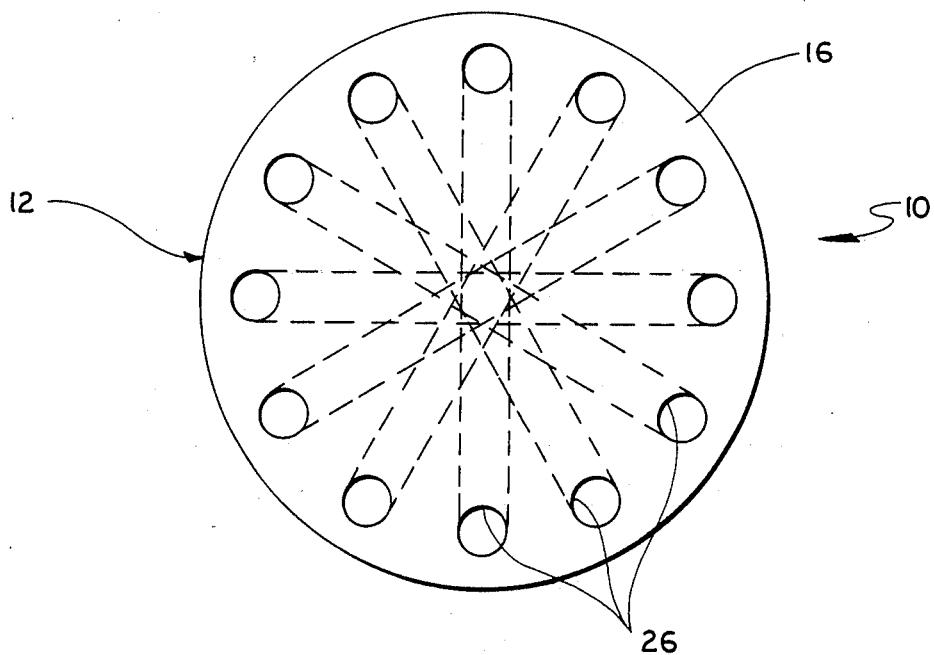
FIG. 2 is an end view of the body member of FIG. 1 showing the access to the plurality of channels.

In the preferred embodiment shown in FIG. 1, the channels 26 are accessible through the spaced apart second end surface 16. FIG. 2 shows in more detail the configuration of the access to the channels 26 at the second end surface 16. The inside diameter of the channels 26 is selected to be compatible with the preselected radiation source 28 that will be used within the device 10. On such radiation source 28 that can be used with the present invention is shown in FIG. 1. It consists of a series of small cylindrical sleeves 30 that look much like beads strung on a wire-like member 32. Each sleeve 30 contains a source of radiation. The overall intensity of the radiation source 28 can be controlled by selecting the number and spacing of such sleeves 30 on the wire-like member 32. Once the number and spacing has been selected, the wire-like member 32 and sleeves 30 can then be encapsulated in a plastic coating 34 to retain the relative spacing. A preselected length of the encapsulated radiation source 28 can be cut and placed inside a clear, flexible, plastic tube 36. This type of radiation source 28 and flexible tube 36 are well known in the art.

The channels 26 must be accessible through at least one surface of the device 10 so that the radiation source 28 inside the flexible tube 36 can then be inserted into the device 10 and positioned at any point along the channel 26. If one such length of radiation source 28 is not sufficient to produce the desired intensity of radiation treatment, a second, third, fourth, or more lengths of radiation source 28 can be prepared with each length being inserted into another channel 26 and positioned in close proximity to the previously inserted radiation sources 28. In this manner, the radiation source 28 can be grouped along one side of the device 10. In a similar manner, sections of the radiation source 28 can be positioned in the dome 14 to provide a radiation source 28 which is located only in the tip of the device 10. This dome-only configuration is particularly useful for application of therapeutic radiation treatment interuterine particularly to such areas as the cervix.

Figure 3:
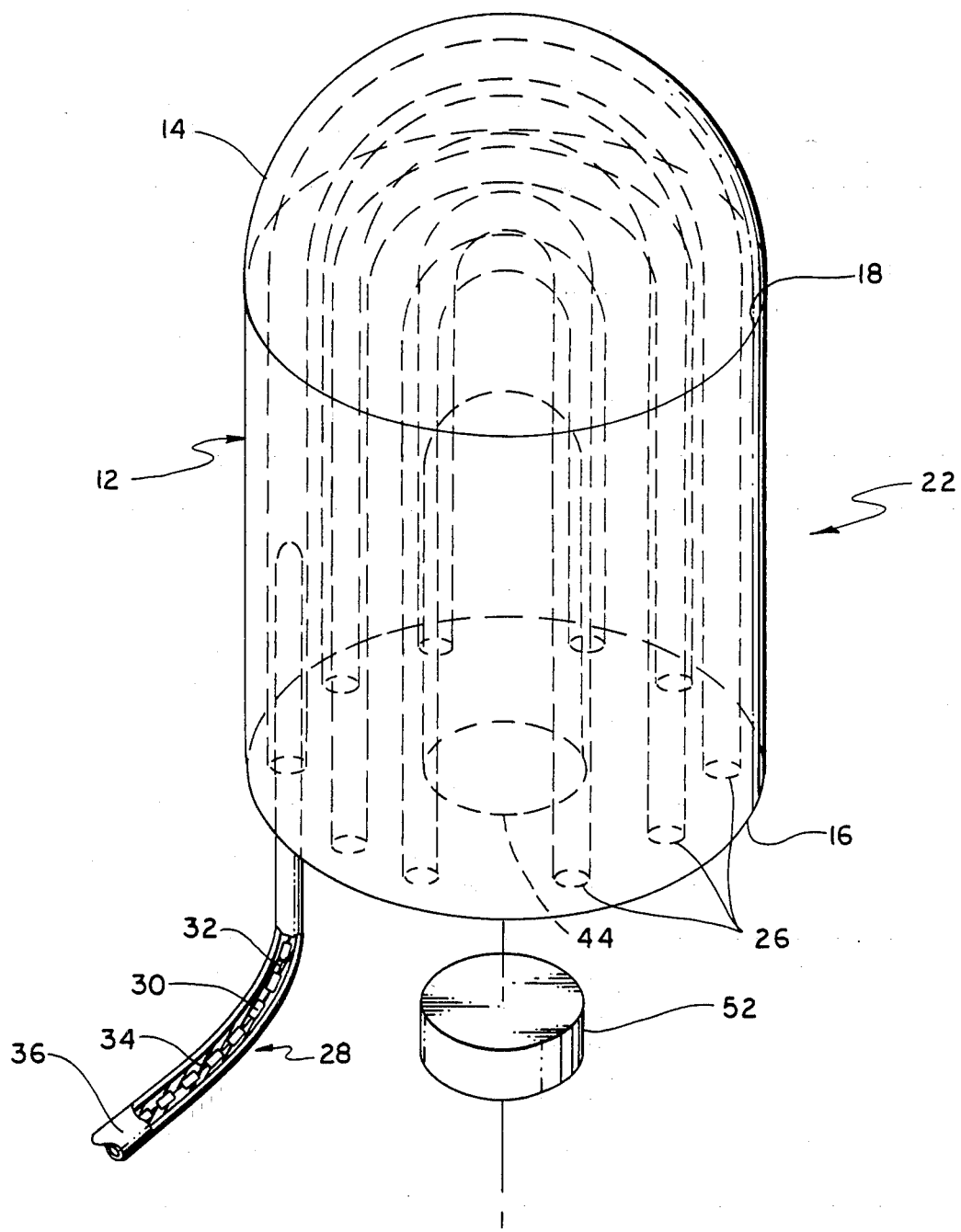
FIG. 3 illustrates another embodiment showing a first attachable body member of an application device having U-shaped channels traversing the body member, an internal central cavity and a radiation source partially inserted into one of the channels.
Figure 5:
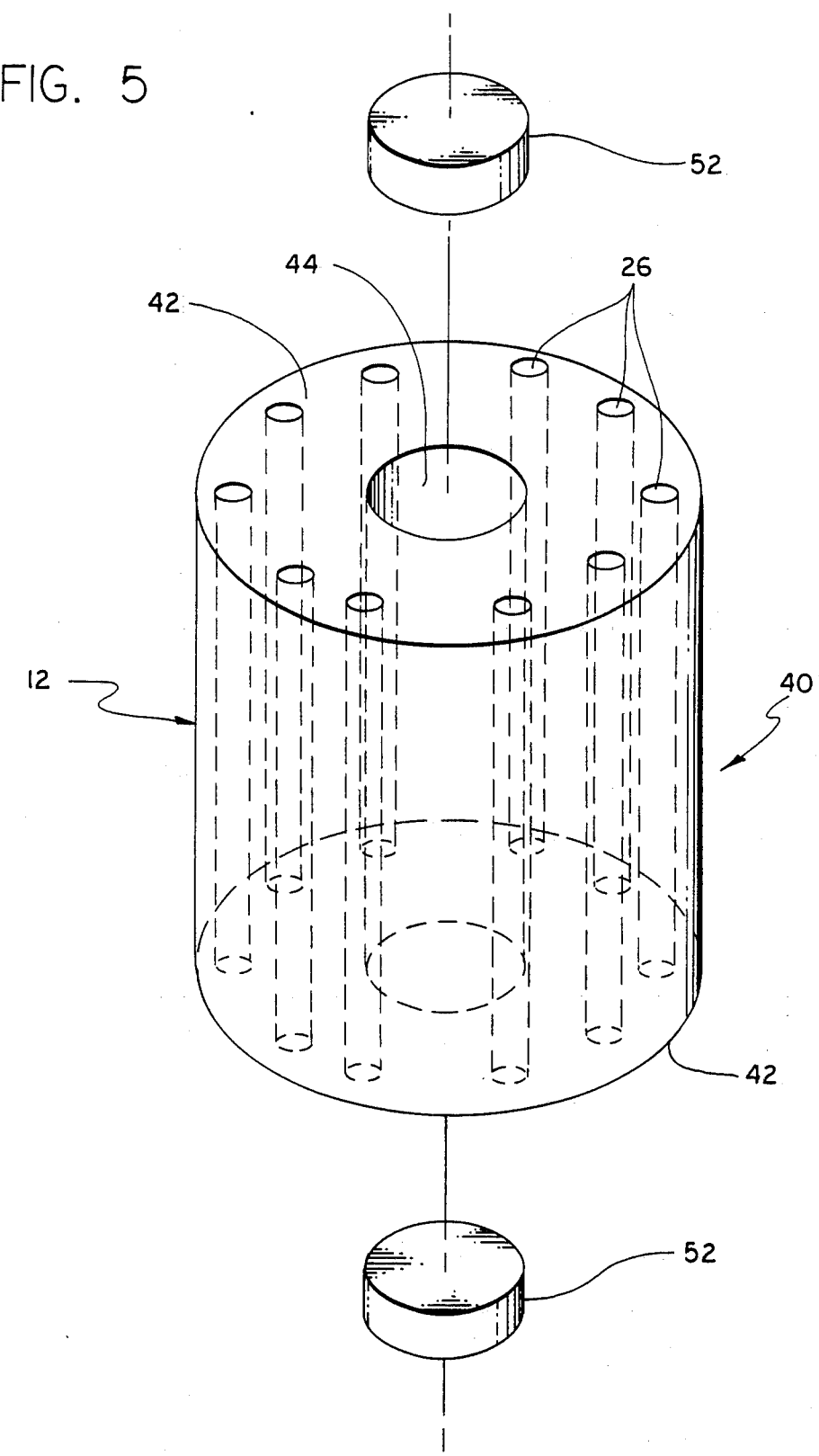
FIG. 5 illustrates the second attachable body member of the application device showing the plurality of internal U-shaped channels and an internal central cavity.

FIG. 3 shows another embodiment, a first attachable body member 22, for applying therapeutic radiation which is similar to the device 10 depicted in FIG. 1. The first attachable body member 22 is constructed of a cylindrical section 12 of a preselected outside diameter and axial length. A dome 14 is mounted on the first end surface 18 of the cylindrical section 12. The first attachable body member 22 has first walls forming an internal central cavity 44 of a preselected inside diameter and length which provides two functions. The first is to produce a first attachable body member 22 which weighs less because of the removal of material to form the central cavity 44. The second function is to provide a surface to which a connector 52 could be attached. The embodiment shown in FIG. 1 was of a variable length depending upon the application of the device. The first attachable body member 22 shown in FIG. 3 is of a selected fixed length which when connected with second attachable body members 40, shown in FIG. 5, is used to construct a device of any desired length. This ability to construct an application device 10 to a preselected length will relieve the user of the burden of warehousing several different lengths of the device 10. The user need only warehouse the first attachable body member 22 and attachable second body members 40 to construct any desired length.

Figure 4:
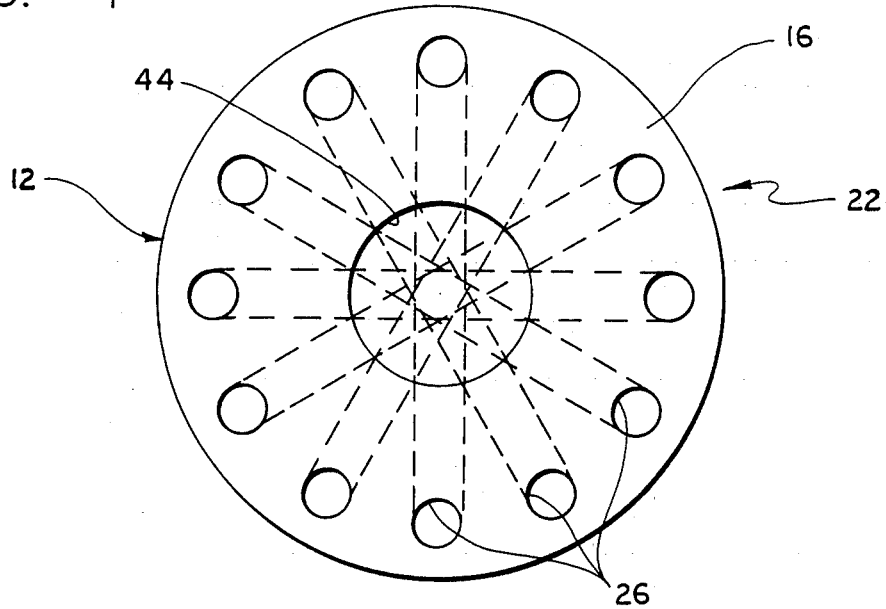
FIG. 4 is an end view of the embodiment of FIG. 3 showing access to the channels and the internal central cavity.

FIG. 4 shows an end view of the first attachable body member 22. In addition to the array of channels 26 spaced around the outside edge, FIG. 4 shows the central cavity 44 as accessible at this second end surface 16.

FIG. 5 depicts an attachable second body member 40 of the device 10. Ths second body member 40 is made up of a cylindrical section 12 with spaced apart end surfaces 42 and walls forming a plurality of channels 26. The axial length of the attachable second body member 40 can be preselected to provide one standard size or an array of lengths. The outside diameter of the attachable second body member 22 should be similar to that of the first attachable body member 22 to provide a smooth transition between the peripheral surfaces of the body members. The channels 26 should be in the same configuration pattern as the channels 26 provided in the first attachable body member 22. This identical channel 26 configuration will allow the channels 26 to be aligned when an end surface 42 of attachable second body member 40 is connected with the second end surface 16 of the first attachable body member 22 shown in FIG. 4. The attachable second body member 40 also has walls forming a central cavity 44 which provides a surface to accept a connector 52. The size of the central cavity 44 is determined by the type of connector 52 selected to attach a first body member 22 to a second body member 40. The length of the central cavity 44 must be selected to accomodate the connector 52 and could be longer in order to reduce the weight of the cylindrical section 12. The same connector 52 can be utilized to attach a second body member 40 to another second body member 40. The location of the central cavity 44 is determined by the type of connector 52 that is utilized. If the central cavity 44 is slightly offset from the center axis of the cylindrical section 12, the insertion of the connector 52 into the central cavities 44 of opposing body members with the peripheral surface of the cylindrical section 12 in alignment will therein align the channels 26 in the connected device 10.

The connector 52 can be chosen from the existing art and take forms such as a double ended bayonet, a keyed and tapered coupling, a screw or a bolt that passes through attachable second body member 40 and is anchored to threads within the central cavity 44 of the first attachable body member 22. If the connected body members are to be reused, the means chosen to connect the body members should be releasable to allow the body members to be taken apart for sterilization.

Figure 6:
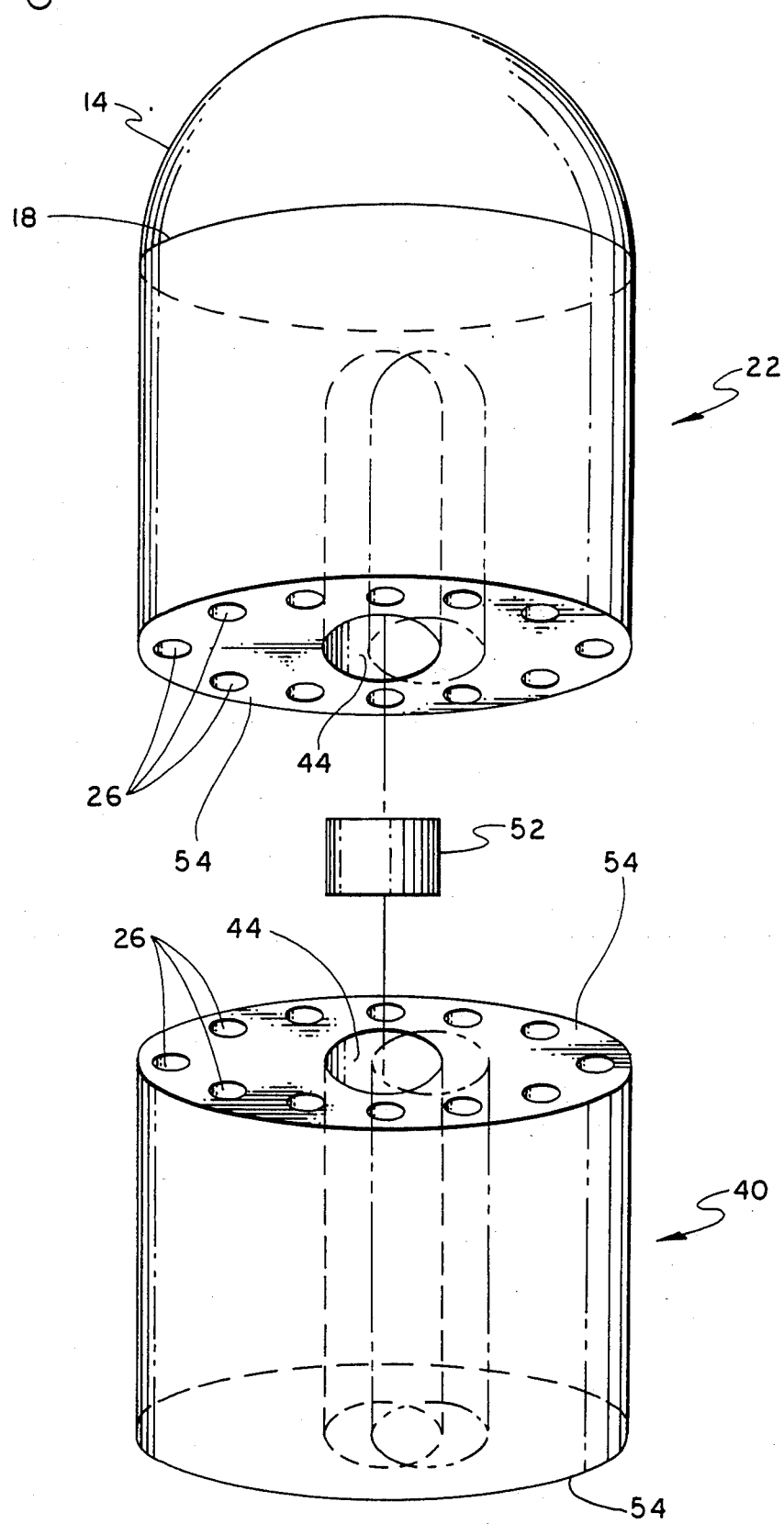
FIG. 6 illustrates another preferred embodiment of the present invention with offset end surfaces.

FIG. 6 depicts yet another embodiment of the first attachable body member 22 and attachable second body member 40. In this embodiment, the offset end surfaces 54 that provide access to the channels 26 and central cavity 44, are formed at other than a right angle to the axis of the peripheral surface of the cylindrical section 12. Thus, the offset surfaces 54 to be connected form an ellipse which allows the body members to be coupled together in a manner that will automatically align the channels 26. Further, after the members are connected together, the last body member of a device 10 can accept the application of a torque and transmit that torque to the next attached section body member the offset connected surfaces 54. This will decrease the chance that a particular connector or body member would slip and allow adjacent body members to rotate relative to each other. Any such rotation might result in displacement of the radiation source 28 and certainly would introduce ambiguity in the orientation of the radiation source 28. Since certain changes may be made in the above device without departing from the scope of the invention herein involved, it is intended that all matter contained in the above description or shown in the accompanying drawings shall be interpreted in an illustrative and not in a limiting sense.

What is claimed is:

1. A device for applying therapeutic radiation from a preselected radiation source to a predetermined portion of a body comprising, in combination: a body member having:
   an external peripheral surface;
   a first end surface; and
   a second end surface spaced from said first end surface;
said body member further comprising:
   at least first internal walls defining a first radiation source receiving channel means spaced a preselected distance from said peripheral surface, and having:
   a first portion extending from said second end surface to regions adjacent said first end surface; and
   a second portion extending from said first portion at said first end surface to said second end surface; and,
   said channel means communicating with regions external said body member at said second surface whereby the radiation source of a preselected intensity inserted at least along a preselected portion of said channel means is applied to the predetermined area of the body requiring therapeutic radiation treatment.

2. The device for applying therapeutic radiation of claim 1 wherein:
said first internal walls define a plurality of spaced apart, non-intersecting channel means.

3. The device for applying therapeutic radiation of claim 1 wherein:
said first end surface is a closed double curved surface.

4. The device for applying therapeutic radiation of claim 3 wherein the closed double curved surface is a dome having a preselected radius.

5. A device for applying therapeutic radiation from a preselected radiation source to a predetermined part of a body comprising a body member means for holding said preselected radiation source, and said body member means having first walls forming a plurality of generally U-shaped channels having a preselected first inside diameter that internally traverse the body member means, said channels being accessible at at least one surface of the body member means whereby said radiation source of a preselected intensity inserted along a preselected portion of a preselected channel is applied in a preselected orientation to the predetermined parts of the body requiring therapeutic radiation treatment.

6. The device for applying therapeutic radiation of claim 5 wherein said generally U-shaped channels form a criss-cross, non-intersecting pattern.

7. The device for applying therapeutic radiation of claim 5 wherein said body member means further comprises:
a first body member section having a preselected outside diameter and length;
a first end surface comprising a closed double curved surface; and,
second end surface spaced from said first end surface.

8. The device for applying therapeutic radiation of claim 5 wherein the body member means further comprises:
a plurality of attachable body members having:
a preselected first outside diameter and first axial length;
a first end surface defining a closed double curved surface;
a spaced apart second end surface; and,
walls defining at least one generally U shaped channel having at least one end accessable at said second end surface
at least one other attachable body member comprising:
a second attachable body member having:
a preselected second outside diameter and second axial length;
with spaced apart end surfaces; and,
walls defining at least one channel extending substantially axially from at least one of said spaced apart end surfaces;
each attachable body member having second walls defining a central cavity within each attachable body member of a preselected second inside diameter and second length being accessable at each of said spaced apart end surfaces; and,
means for connecting said plurality of attachable body members by said central cavities in generally channel alignment to provide a preselected length whereby the connected attachable body members can be inserted a preselected depth into a predetermined body cavity.

9. The device for applying therapeutic radiation of claim 8 wherein the connected spaced apart end surfaces of the attachable body members form ellipses.

10. The device for applying therapeutic radiation of claim 8 wherein the closed double curved surface is a dome having a preselected radius.

11. A device for applying therapeutic radiation from a preselected radiation source to a predetermined part of a body comprising, in combination:
a body member having:
a cylindrical section of a preselected outside diameter and length;
a first end surface forming a closed double curved surface; and,
a spaced apart second end, said body member further comprising:
first walls defining a plurality of generally Ushaped channels having a preselected first inside diameter;
the channels internally traversing the cylindrical section and closed double curved surface; and,
the channels being accessible through said spaced apart second end surface of said cylindrical section whereby said radiation source of a preselected intensity inserted along a preselected portion of a preselected channel is applied in a preselected cylindrical section orientation to any accessible area of the body requiring therapeutic radiation treatment.

12. The device for applying therapeutic radiation of claim 11 wherein said generally U-shaped channels form a criss-cross, non-intersecting pattern.

13. The device for applying therapeutic radiation of claim 11 wherein the closed double curved surface is a dome having a preselected radius.

14. A device for applying therapeutic radiation from a preselected radiation source to a predetermined part of a body comprising, in combination:
a first attachable body member having:
a first cylindrical section having:
a first preselected outside diameter;
first axial length; and,
opposing ends;
a dome of preselected radius mounted on the first opposing end of the cylindrical section;
first internal walls forming a central cavity of a preselected first inside diameter and second length within the cylindrical section being accessible at said second opposing end;
second internal walls forming a plurality of U-shaped channels having a preselected second inside diameter that internally traverse the cylindrical section and dome between the central cavity and external peripheral surface of the first body member, said channels being accessible at said second opposing end;
a plurality of second attachable body members having:
a second cylindrical section having:
a second preselected outside diameter each having a preselected axial length; and,
opposing ends;
third walls forming a central cavity within each second attachable body member of a preselected third inside diameter and third length, being accessible at each of said spaced apart end surfaces;

fourth walls forming a plurality of channels of a preselected fourth inside diameter that traverse each second attachable body member from one spaced apart end surface to the other spaced apart end surface between the central cavity and the peripheral cylindrical surface such that the channels of each second attachable body member are alignable with the channels of the first attachable body member; and, means for connecting one attachable body member to another attachable body member by the central cavity with the central cavities of the attached body members located in connecting means channel alignment whereby said radiation source of a preseleced intensity inserted along a preselected portion of any channel in any attached body member is applied in a preselected orientation to any accessible area of the body requiring therapeutic radiation treatment.

15. The device for applying therapeutic radiation of claim 14 wherein connected surfaces of the attachable body members form ellipses.

16. The device for applying therapeutic radiation of claim 14 wherein the channels form a criss-cross, non-intersecting pattern.

17. The device for applying therapeutic radiation of claim 14 wherein the central cavity of the first attachable body member and central cavity of the second attachable body member are offset from the central axis of the cylinder section to allow the inserting into the central cavities of the means for connecting sections in channel alignment connection.

* * * * *